United States Patent [19]

Aronsohn

[11] Patent Number: 4,662,356

[45] Date of Patent: May 5, 1987

[54] DEVICE AND METHOD FOR MINIMIZING IMPLANT EFFECTS

[76] Inventor: Valerie M. Aronsohn, 10571 Wyton Dr., Los Angeles, Calif. 90024

[21] Appl. No.: 807,961

[22] Filed: Dec. 12, 1985

[51] Int. Cl.⁴ ............................................. A61B 17/28
[52] U.S. Cl. .................................... 128/1 R; 128/346; 128/303 R
[58] Field of Search ................. 128/1 R, 25, 425, 346, 128/303 R, 321, 59, 60, 61; 604/304, 74

[56] References Cited

U.S. PATENT DOCUMENTS

| | | | |
|---|---|---|---|
| 183,602 | 10/1876 | Strubell | 128/346 |
| 4,164,223 | 8/1979 | Munib | 128/321 |
| 4,205,681 | 6/1980 | Nestor et al. | 128/319 |
| 4,249,534 | 2/1981 | Muldrow, Jr. | 128/319 |
| 4,502,485 | 3/1985 | Burgin | 128/321 |

OTHER PUBLICATIONS

Duane L. Larson, M.D., "The Prevention and Correction of Burn Scar Contracture and Hypertropy", Shriners Burns Institute, University of Texas Medical Branch, Galveston, Texas, copyrighted 1973.

Primary Examiner—C. Fred Rosenbaum
Assistant Examiner—Gene B. Kartchner
Attorney, Agent, or Firm—Bogucki, Scherlacher, Mok & Roth

[57] ABSTRACT

A method and device effective for inhibiting the contracture of scar tissue following breast implantation, comprising a pair of pivotally coupled arms for contacting the breast on opposite sides and applying static pressure thereto. Each arm includes a curved bottom portion that extends around the lower surface of the breast means and includes means for adjusting the pivot point of the arms in relation to the size of the breast. The upper ends of the arms extend above the breast and means connect the arms to adjust the pressure of the side portions against the breast.

13 Claims, 5 Drawing Figures

DEVICE AND METHOD FOR MINIMIZING IMPLANT EFFECTS

BACKGROUND OF THE INVENTION

The present invention relates to elimination or minimization of scar tissue contracture resulting from cosmetic surgery, and more particularly is directed to assuring that the scar tissue that forms following breast implantation will not contract within the breast to cause hardness, pain or asymmetry.

Plastic surgery involving breast implantation by silicone injection is well known and was once widely practiced but is no longer in vogue. Preferred techniques now use implantation of an enclosed silicone gel. In the breast implantation operation, the sac implant of circular outline is introduced, in one common approach, into the breast via a semi-lunar incision around the areola. Because the implant is a foreign object the body builds a layer of scar tissue around the implant to seek to wall it off from the surrounding tissues. A circular internal scar, which is initially soft, forms about the outline of the sac. However, because scar tissue tends to contract in a linear dimension, there is a subsequent tendency to internal contracture in a ring-like pattern around the implant. Scar contracture results in breast hardening, sometimes asymmetry, and occasionally causes pain by distorting nerves in the region. Unless the scar tissue area is vigorously massages on a regular basis scar tissue contracture can take place. Accordingly, it has been the practice for women following breast implantation to require post-operative treatment by a physician or medical aide. The doctor must advise the patient to massage and compress the breast vigorously on a daily basis for a period of time in an effort to insure that the breast stays soft and to inhibit the scar tissue contracture that takes place.

However, this procedure is very time consuming for the patient. Women usually cannot exert the force that strong professional hands can apply, and they may be uncertain of the particular actions that must be undertaken. Moreover, dormant scar tissue can be reactivated and commence contracture again under stressful circumstances, such as infection or some illness. Also it may be required under some circumstances of contracture for a doctor to use a manual capsulotomy procedure, physically breaking down contracted scar tissue. When this is done against strongly resisting tissue the gel implant can also burst or commence leaking, requiring emergency procedures to evacuate the fluid.

A need therefore exists for some means, readily usable, which is effective for preventing the breasts from hardening due to scar contracture following implantation. Such means should soften scar tissue following breast implantation and be effective under a variety of circumstances. Further it must be simple, relatively inexpensive, adjustable for use regardless of the individual's physique, and readily and conveniently applicable by the patient. It must manipulate and apply pressure to the breast in such fashion that the requisite forces act to prevent the contracture of scar tissue without other adverse effects.

SUMMARY OF THE INVENTION

Methods and apparatus in accordance with the invention stretch the circular scar tissue formed after breast implantation by periodically applying continuous consistent pressure for selected intervals in a manner that inhibits contracture. Laterally directed compressive forces, steadily applied for substantial time intervals on a daily basis, act to repetitively deform the scar tissue in a direction opposite to the tendency to contract, and prevent contracture. The device and method can also be used to prevent reactivation and in many instances to stretch scar tissue previously contracted. With a very firm breast the device can be applied for 30 minutes on the breast and will stretch the scar, making manual capsulotomy easier.

A device effective for inhibiting scar contracture following breast implantation comprises a breast compressor defined by a pair of arm members pivotable about an adjustable pivot point. The arm members each include side pads or contact areas for squeezing the breast laterally and perpendicularly in the scar tissue plane and applying pressure to stress and stretch the scar. The arms include curved, diverging, bottom portions that are adapted to pass around the lower surface of the breast without engagement as pressure is applied. The bottom portions include a number of spaced apart pivot pin holes for adjusting the pivot position in relation to the size of the breast. The arm members are configured so that pressure can be exerted laterally on the breast without interference or pinching in the pivot region. A pair of free ends extend upwardly from the arms of the device and are also shaped with curvatures so as to be non-interfering as compression is applied. Means are provided for drawing and engaging the free ends to adjust and hold the breast in compression by drawing the side pads together to a desired spacing.

The means for adjusting the pivot position for the arms can comprise a threaded pin and sleeve fitting through the structure in the bottom portion. The means for adjusting the contact pressure of the side portions against the breast, can be, for example, a flexible string or band connected between the upper ends of the arms and means on the string and arms for selectively controlling the tightness of the squeeze of the side portions against the breast. Such a string, for example, can include spaced apart beads engaging in restricted slots in the arm ends for controlled application of continued pressure against the breast by locking to a given position.

BRIEF DESCRIPTION OF THE DRAWINGS

The invention will be more clearly understood by reference to the detailed description below, taken in connection with the accompanying drawings, in which.

DETAILED DESCRIPTION OF THE INVENTION

The method of inhibiting contracture of scar tissue following breast implantation is, in accordance with the invention, based upon periodic application of substantial lateral pressure for a significant duration. The lateral pressure is typically exerted against the sides of the breast, deforming substantially the entire breast by compressing the sides while forcing the top and bottom portion outwardly. All of the interior ring-like or circular scar tissue is thus acted upon, being placed under substantial tension along the scar line whether being deformed inwardly or outwardly. The pressure exerted is well within the limits that can be sustained by the implant sac so that there is a minimal danger of rupture or internal leakage. The forces that can be exerted are well below the pain threshold, but substantially above what can be applied manually. The forces are exerted by side contact members and although considerable pressure is applied and distortion is substantial, the procedure is not painful. Thus the constant tendency of internal scar tissue to contract along the scar line is effectively opposed by the periodic deformation. Compression is maintained for 15-30 minutes per application, three times a day for the first six months and once daily thereafter. The forces are most conveniently applied laterally, in the horizontal direction for an upright person, but in some instances it can be efficacious to apply the forces vertically.

Application several times each day for a period of six months following breast implantation and daily thereafter is generally sufficient to inhibit scar tissue contracture. Inhibit in this sense does not preclude the possibility of scar reactivation, by illness or other traumatic causes. If such occurs, however, reinstitution of the compression procedure will generally cause the scar tissue to stretch and resoften a breast that is becoming firm. Where scar tissue has contracted, and must be subjected to manual capsulotomy, which breaks down the scar tissue by the application of high, concentration forces, the use of the present compression method prior to manual capsulotomy is generally found to make the latter procedure easier to perform successfully.

Figure 1:
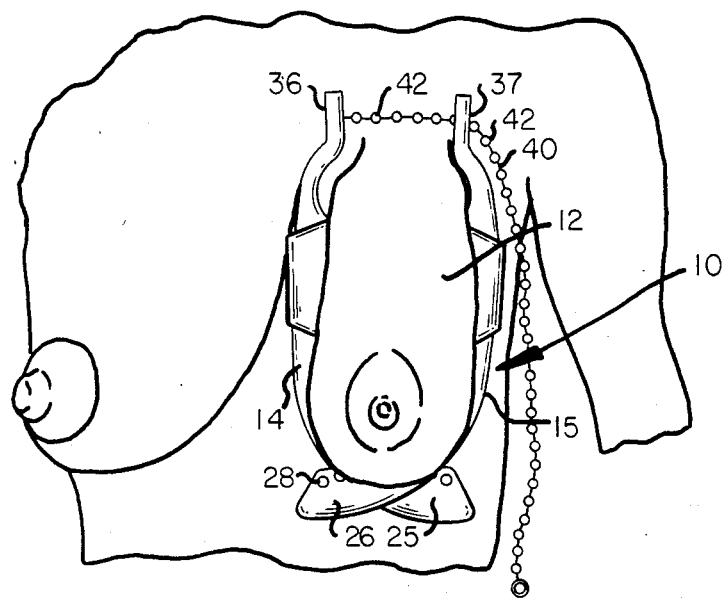
FIG. 1 is a perspective view of a scar contracture inhibitor device according to the invention as applied to a breast after implantation.
Figure 4:
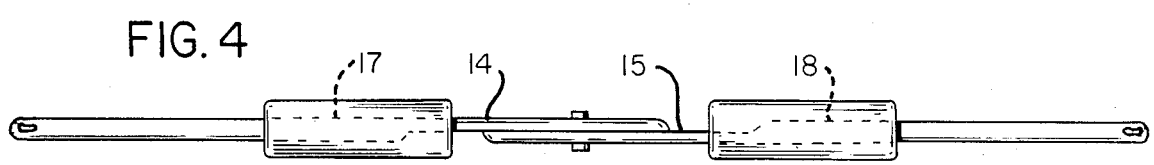
FIG. 4 is a bottom view of the device of FIG. 1.
Figure 5:
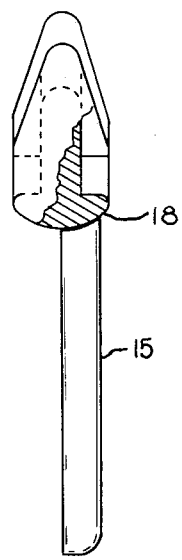
FIG. 5 is an end view, partly in section, of the device of FIG. 1.
Figure 2:
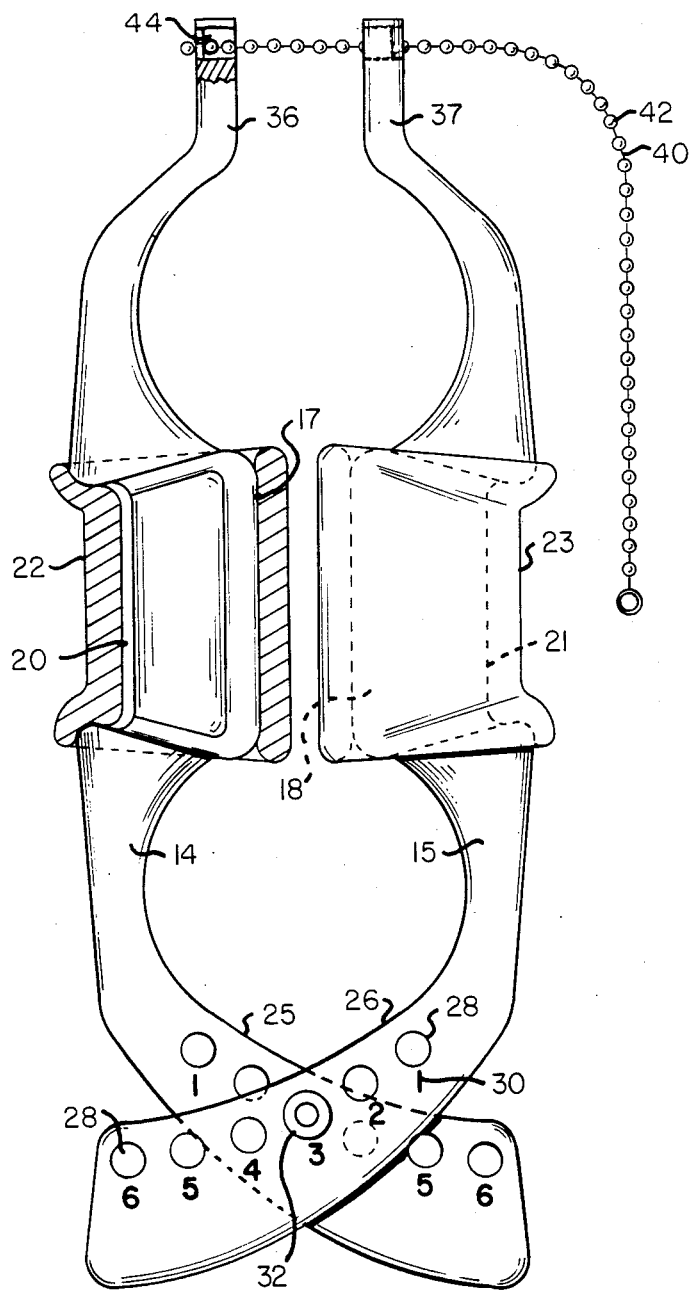
FIG. 2 is a front view of the device of FIG. 1.

A device 10 for use in accordance with the method is shown in FIGS. 1-4, to which reference is now made. The device 10 is shown as applied to the left breast 12 of a subject who has previously received a breast implant (not shown). The incision is typically made around the areola and the implant is placed within the pocket created. Scar tissue forms in a ring-like fashion and in a plane parallel to the front of the chest wall. The device 10 comprises a pair of arm members 14, 15 formed integrally to define different sections, and being substantially alike so that extra molds are not needed. In an intermediate region of each arm member 14, 15, is disposed a side or pressure pad 17, 18 respectively (best seen in FIGS. 2 and 3). The side pads 17, 18 face each other, with facing surfaces that lie in vertical planes and are approximately ¾" wide by 2.0" high. The areas of the side pads 17, 18 distribute the forces for comfortable, non-painful application. Smaller side pads, a number of small contact surfaces, or other expedients may be used depending on the purpose of use, pain threshold and other factors. The side pads lie on inwardly protruding portions of the arm members 14, 15 so as to avoid interference of the arms with other parts of the breast when compression is applied. In this intermediate region, each arm member includes an inset portion 20, 21 along its outer periphery, for firmly receiving a stretchable encircling cover pad 22, 23 respectively for further extending the area of contact and providing a cushioning effect. Advantageously, these cover pads 22, 23 are of tubular rubber or other elastomer, although they may also be of other suitable cushioning materials, such as fabric covered foam, that can be stretched over the pad and seated in the insets 20, 21. The outer margins of the arms 14, 15 in the intermediate region are approximately linear, apart from the insets 20, 21. The inner edges however curve outwardly and then back toward the opposing arm along approximately circular arc segments in both the bottom and upper regions (as seen in FIGS. 1 and 2). These curvatures provide substantial clearance both above and below the breast that is to be compressed by the side pads 17, 18 and cover pads 22, 23. The bottom portions of the arms 14, 15, comprise diverging extensions 25, 26 which cross adjacent a pivot axis. To establish the pivot axis, each diverging extension 25, 26 includes a sequence of spaced apart pivot holes 28 having an adjacent number 30 molded into or fixed on the plastic. Dependent on the span of the breast to be compressed, a removable pivot is defined by an internally threaded sleeve 32 inserted into a selected pivot hole 28. An externally threaded pin or screw 34 is removably coupled into the sleeve 32. The surface numbers 30 make it convenient to match up the pivot holes so as to provide a symmetrical geometry, in which the side or pressure pads 17, 18 act directly and perpendicularly against the sides of the breast.

Figure 3:
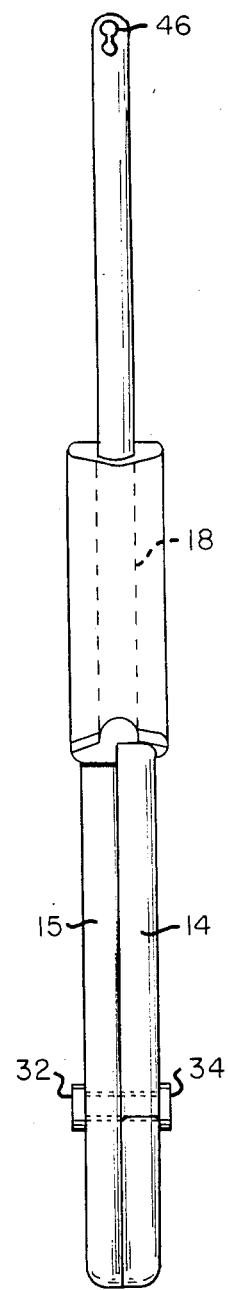
FIG. 3 is a side view of the device of FIG. 1.

At the upper end, each arm 14, 15 curves inwardly to a free end 36, 37 which is substantially vertical and includes means for seating a retainer, such as a high strength "Nylon" string or band 40 having integrally molded beads 42. The upper end 36 of one arm 14 includes an elongated slot 44 having an upper opening larger than the beads 42 and a narrow bottom end into which the string 40 is slidable, but which is smaller than the beads 42. When the string 40 is slid down into position a conforming plug (not shown) may be inserted and adhesively secured to the slot 44 walls to provide positive backing of the one end of the string 40. The engaged bead 42 within the small part of the slot 44 retains the string 40 against reactive forces exerted in the perpendicular direction by the compressed breast. The upper end 37 of the other arm 15, as seen in FIG. 3, has a similar slot 46 with an opening at its top end larger than at its bottom portion, but which is not closed by a plug. The slot 46 thus permits the string 40 to be pulled so as to draw the arms 14, 15 together, then to draw the string 40 and beads 42 down into the small part of the slot 46, preventing release.

In use, the patient places the device 10 against the chest wall encircling the breast and around the base of the breast 12 in FIG. 1, with the somewhat semicircular diverging bottom extensions 25, 26 free of close contact with the lower surface of the breast 12. The two side pads 17, 18 and covering members 22, 23 are then brought together into tight contact with the opposite sides of the breast 12. In this position compressive pressure is exerted symmetrically and in opposition in the plane of the ring-like scar tissue. If the breast is too large or small the pivot position can be adjusted by replacement of the pivot sleeve 32 and pin 34 into different matched pivot holes 28.

With a desired force of compression established by pulling the string 40 end to bring the arms 14, 15 together, the free end of the string 40 is brought down into the slot 46 in the upper end 37 and the device 10 is then locked into position. When it is desired to release the pressure on the breast 12 and remove the device 10, the string 40 is merely pulled upwardly out of the small end of the slot 46. This permits the arms 14, 15 and the contact padss 22, 23 to move outwardly, thus permitting removal of the device from the breast.

When applied, the breast compressor provides a consistent pressure to the breast, more than can be produced by the patient herself. The configuration avoids pinching and interference both above and below the contact areas. The use of the breast compressor approach also avoids the problem of long nails when the patient massages the breasts by hand. With firm pressure the nails dig into the breast tissue, causing pain. If the breast is already starting to become firm, the breast compressor may help soften it by continuous use, and will soften scar tissue around the breast, which causes the hardness and often asymmetry of the breast. The amount of pressure applied to the breast can be adjusted to control the tightness of the squeeze, by bringing in or letting out the beaded string or band. It will be recognized that other cushioning pads and other tightening means, such as elastic bands, can be employed with this device.

The breast compressor can be used by the patient herself to apply pressure to the breast each time for a period say from about 15 to 25 minutes several times a day for a period of for example six months following breast implantation. Used once daily thereafter it properly maintains the breast in a soft condition and opposes scar tissue contracture, without the aid of a physician. To save time, two breast compressors can be employed simultaneously, one on each breast.

From the foregoing, it is seen that the invention provides a simple breast compressor device formed of only a few components, and which can be readily used by a patient for maintaining the breast soft and breaking down and stretching scar tissue following breast implantation.

Since further changes and modifications of the invention will occur to and can be made readily by those skilled in the art without departing from the invention concept, the invention is not to be taken as limited except by the scope of the appended claims.

What is claimed is:

1. The method of preventing internal scar tissue from contracting to harden after cosmetic breast surgery is performed in which an incision is made for implantation of inert matter comprising the steps of:
    mechanically compressing opposite sides of the breast in the plane of the implant and parallel to the internal scar regions building about the implant;
    maintaining static pressure on the opposite sides of the scar regions sufficient to stretch a ring-like line of scar tissue about the implant without rupturing scar capsules;
    maintaining the static pressure for a time period in excess of fifteen minutes to soften scar tissues about the implant in response to the stretching; and
    repeating the procedure approximately several times daily for six months or more following implantation.

2. The method as set forth in claim 1 above, wherein the mechanical compression is applied to opposite sides of the breast in the horizontal direction relative to a standing subject, and substantially perpendicularly to the sides of the breast.

3. The method as set forth in claim 2 above, wherein the mechanical compression is applied to the breast over an area on each side for fifteen to twenty-five minutes three times daily for six months, and wherein the compression is repeated daily after the six month interval.

4. A device effective for preventing scar tissue contracture following breast implantation to maintain the breast soft, which comprises:
    a pair of arms having a common pivot point and side surfaces for contacting the opposite sides of the breast in the scar region;
    each arm including a curved bottom portion having a curvature sufficiently large to pass around the lower surface of the breast, the curved bottom portions including means for adjusting the common pivot point of said arms in relation to he size of the breast;
    each arm also including an upper portion extending upwardly along the side portions; and
    means connecting the upper portions of said arms to adjust the pressure of said side portions against the breast.

5. The device of claim 4, each of said arms including enlarged contact pads on the side surfaces and facing opposite sides of the breast in a substantially normal direction thereto.

6. The device of claim 4, said curved bottom portion comprising a substantially semicircular bottom member integral with the side portions.

7. The device of claim 5, said curved bottom portion formed of two symmetrical half portions each connected to a side portion, the outer ends of said half portions being overlying, said means for adjusting the pivot point comprising a number of spaced apart symmetrically placed pivot holes in said overlying half portions and pivot pin means for engaging in a selected pair of holes.

8. The device of claim 4, said pressure adjusting means comprising string means connected between the upper portions of said arms for selectively adjusting the tightness of the squeeze of said side portions against the breast.

9. The device of claim 4, including soft flexible material encompassing said pads and covering the inner surfaces of said pads.

10. A device effective for softening the breast by stretching scar tissue formed following breast implantation, which comprises:
    a pair of upwardly extending arms having a crossing region;
    a pair of inwardly extending contact members each connected to a different arm, for contacting opposite sides of the breast and applying pressure thereto;
    a pair of substantially semicircular bottom members each integrally connected to a different one of said arms to define the crossing region and adapted to be positioned around the lower portion of the breast;
    pivot pin means on said bottom members for providing an adjustable pivot point for said bottom members in relation to the size of the breast;
    a pair of upwardly extending arm extensions having spaced apart sections at their upper ends, integrally connected to said arm; and
    adjustable tightening means coupling the upper ends of the arms for drawing the arms inwardly together for selectively controlling the amount of pressure applied to the breast by the inwardly extending contact members on said side portions.

11. The device of claim 10, said bottom members being formed of two symmetrical half portions, and each having a number of spaced apart holes, wherein the pivot pin means comprises a detachable pivot pin positioned in a selected pair of holes in the two bottom members.

12. The device of claim 10, said adjustable tightening means comprising a string having spaced apart beads connected at one end to the upper end of one of said arms, the other arm having a slot in the upper end for receiving the string and engaging a bead in said string to maintain a selected pressure against the breast.

13. The breast compressor of claim 10, said arms including the contact members, bottom members and upper extensions being formed integrally of plastic.

* * * * *